United States Patent
Kapadia

(10) Patent No.: US 11,188,069 B2
(45) Date of Patent: Nov. 30, 2021

(54) PREVENTATIVE MAINTENANCE OF ROBOTIC SURGICAL SYSTEMS

(71) Applicant: Covidien LP, Mansfield, MA (US)

(72) Inventor: Jaimeen Kapadia, Cambridge, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/638,963

(22) PCT Filed: Aug. 16, 2018

(86) PCT No.: PCT/US2018/000288
§ 371 (c)(1),
(2) Date: Feb. 13, 2020

(87) PCT Pub. No.: WO2019/036003
PCT Pub. Date: Feb. 21, 2019

(65) Prior Publication Data
US 2020/0363795 A1   Nov. 19, 2020

Related U.S. Application Data

(60) Provisional application No. 62/546,349, filed on Aug. 16, 2017.

(51) Int. Cl.
*G05B 23/02* (2006.01)
*A61B 34/37* (2016.01)
(Continued)

(52) U.S. Cl.
CPC .......... *G05B 23/0283* (2013.01); *A61B 34/37* (2016.02); *B25J 19/0066* (2013.01);
(Continued)

(58) Field of Classification Search
CPC .. A61B 2017/00119; A61B 2034/2048; A61B 2034/2059; A61B 2090/0803;
(Continued)

(56) References Cited

U.S. PATENT DOCUMENTS

| | | | |
|---|---|---|---|
| 4,996,975 | A | 3/1991 | Nakamura |
| 5,313,935 | A | 5/1994 | Kortenbach et al. |

(Continued)

FOREIGN PATENT DOCUMENTS

| | | | |
|---|---|---|---|
| JP | 2014114111 A | | 6/2014 |
| WO | 02065933 A2 | | 8/2002 |
| WO | 2017090924 A1 | | 6/2017 |

OTHER PUBLICATIONS

International Preliminary Report on Patentability issued in corresponding International Appl. No. PCT/US2018/000288 dated Feb. 27, 2020 (6 pages).

(Continued)

*Primary Examiner* — John H Le
(74) *Attorney, Agent, or Firm* — Carter, DeLuca & Farrell LLP

(57) ABSTRACT

A method of conducting preventative maintenance on a robotic surgical system is provided. The method includes sensing an audio output generated by one or more components of a robotic surgical system with a sensor coupled to the robotic surgical system, converting the audio output into audio output data, comparing the audio output data to a predefined audio data stored in a memory device that is coupled to the robotic surgical system, and selectively outputting a preventative maintenance signal based on a comparison of the audio output data and the predefined audio data.

20 Claims, 4 Drawing Sheets

(51) Int. Cl.
*B25J 19/00* (2006.01)
*G05B 19/4063* (2006.01)
*G06Q 10/00* (2012.01)
*A61B 17/00* (2006.01)

(52) U.S. Cl.
CPC ......... *G05B 19/4063* (2013.01); *G06Q 10/20* (2013.01); *A61B 2017/00119* (2013.01); *G05B 2219/45117* (2013.01)

(58) Field of Classification Search
CPC .... A61B 2090/0807; A61B 2090/0809; A61B 34/30; A61B 34/37; B25J 19/0066; G05B 19/4063; G05B 2219/45117; G05B 23/0283; G06Q 10/20
USPC .......................................................... 702/184
See application file for complete search history.

(56) References Cited

U.S. PATENT DOCUMENTS

| | | | |
|---|---|---|---|
| 5,382,885 A | 1/1995 | Salcudean et al. | |
| 5,400,267 A | 3/1995 | Denen et al. | |
| 6,436,107 B1 | 8/2002 | Wang et al. | |
| 6,611,793 B1 | 8/2003 | Burnside et al. | |
| 7,065,490 B1* | 6/2006 | Asano | G10L 13/033 318/568.12 |
| 9,031,779 B2 | 5/2015 | Djugash | |
| 2001/0013764 A1 | 8/2001 | Blumenkranz et al. | |
| 2002/0032452 A1 | 3/2002 | Tierney et al. | |
| 2002/0188173 A1 | 12/2002 | Kobayashi | |
| 2003/0004610 A1 | 1/2003 | Niemeyer et al. | |
| 2003/0125717 A1 | 7/2003 | Whitman | |
| 2003/0208196 A1 | 11/2003 | Stone | |
| 2005/0131390 A1 | 6/2005 | Heinrich et al. | |
| 2005/0183656 A1 | 8/2005 | Isaacson et al. | |
| 2007/0083286 A1 | 4/2007 | Kobayashi | |
| 2007/0142969 A1 | 6/2007 | Devengenzo et al. | |
| 2007/0151391 A1 | 7/2007 | Larkin et al. | |
| 2007/0156285 A1* | 7/2007 | Sillman | A61B 34/30 700/245 |
| 2007/0203481 A1 | 8/2007 | Gregg et al. | |
| 2008/0167671 A1 | 7/2008 | Giordano et al. | |
| 2009/0090763 A1 | 4/2009 | Zemlok et al. | |
| 2009/0248038 A1 | 10/2009 | Blumenkranz et al. | |
| 2010/0011251 A1 | 1/2010 | Mannar et al. | |
| 2011/0034910 A1 | 2/2011 | Ross et al. | |
| 2011/0257480 A1 | 10/2011 | Takahashi et al. | |
| 2011/0295270 A1 | 12/2011 | Giordano et al. | |
| 2012/0203269 A1 | 8/2012 | Katsuki et al. | |
| 2014/0052135 A1 | 2/2014 | Aman et al. | |
| 2014/0266591 A1 | 9/2014 | Klammer et al. | |
| 2014/0266713 A1 | 9/2014 | Sehgal et al. | |
| 2014/0358453 A1 | 12/2014 | Kirk | |
| 2015/0173838 A1 | 6/2015 | Murphy et al. | |
| 2015/0213417 A1 | 7/2015 | Kuffner, Jr. et al. | |
| 2015/0272575 A1 | 10/2015 | Leimbach et al. | |
| 2015/0297200 A1 | 10/2015 | Fitzsimmons et al. | |
| 2015/0328774 A1 | 11/2015 | Yajima et al. | |
| 2016/0066910 A1 | 3/2016 | Baber et al. | |
| 2016/0249916 A1 | 9/2016 | Shelton, IV et al. | |
| 2016/0256162 A1 | 9/2016 | Shelton, IV et al. | |
| 2016/0256184 A1 | 9/2016 | Shelton, IV et al. | |
| 2016/0256185 A1 | 9/2016 | Shelton, IV et al. | |

OTHER PUBLICATIONS

International Search Report and Written Opinion of the International Searching Authority issued in corresponding International Appl. No. PCT/US2018/000288 dated Jan. 17, 2019 (8 pages).
Extended European Search Report for application No. 18846120 dated May 4, 2021.

* cited by examiner

PREVENTATIVE MAINTENANCE OF ROBOTIC SURGICAL SYSTEMS

CROSS-REFERENCE TO RELATED APPLICATIONS

This application is a National Stage Application of PCT Application Serial No. PCT/US2018/000288 under 35USC § 371 (a), filed Aug. 16, 2018, which claims benefit of and priority to U.S. Provisional Patent Application Ser. No. 62/546,349 filed Aug. 16, 2017, the disclosures of each of the above-identified applications are hereby incorporated by reference in their entirety.

BACKGROUND

Robotic surgical systems have been used in minimally invasive medical procedures since they provide many benefits such as increased accuracy and expediency. However, as with any mechanical or electromechanical system, the components of a robotic surgical system have limited health or longevity. In particular, a robotic surgical system, or components thereof, may become inefficient or even fail due to various factors imposed on the components of the robotic surgical system. For example, prolonged use or applied stress can expedite or cause component failure. Given that these factors and their effects often vary, the lifespan or failure juncture of components of a robotic surgical system can be difficult to predict.

SUMMARY

Accordingly, there is a need for conducting preventative maintenance for a robotic surgical system, or components thereof, to more accurately predict failures and improve efficiencies and effectiveness of the robotic surgical system.

In accordance with one aspect of the present disclosure, a method of conducting preventative maintenance on a robotic surgical system is provided. The method includes sensing an audio output generated by one or more components of a robotic surgical system with a sensor coupled to the robotic surgical system, converting the audio output into audio output data, comparing the audio output data to a predefined audio data stored in a memory device that is coupled to the robotic surgical system, and selectively outputting a preventative maintenance signal based on a comparison of the audio output data and the predefined audio data.

Sensing the audio output may include sensing a first audio output generated by an instrument drive unit of a robotic surgical system. Sensing the first audio output may include sensing fan noise of the instrument drive unit. The method may further include maintaining the sensor coupled to the instrument drive unit.

In one aspect of the present disclosure, converting the audio output into the audio output data may include converting the audio output from an analog signal to a digital signal that can be electrically communicated to a control device of the robotic surgical system.

Sensing the audio output data may include recording the audio output with a microphone.

In some aspects of the present disclosure, selectively outputting the preventative maintenance signal may include determining whether the comparison requires outputting the preventative maintenance signal based upon a comparison value.

In certain aspects of the present disclosure, sensing the audio output may include sensing the audio output with a plurality of sensors coupled to the robotic surgical system. Comparing the audio output data to the predefined audio data may include comparing the audio output data from a first sensor of the plurality of sensors to the predefined audio data to generate a first comparison and comparing the audio output data from a second sensor of the plurality of sensors to the predefined audio data to generate a second comparison. The method may further include generating the comparison value based on the first and second comparisons.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
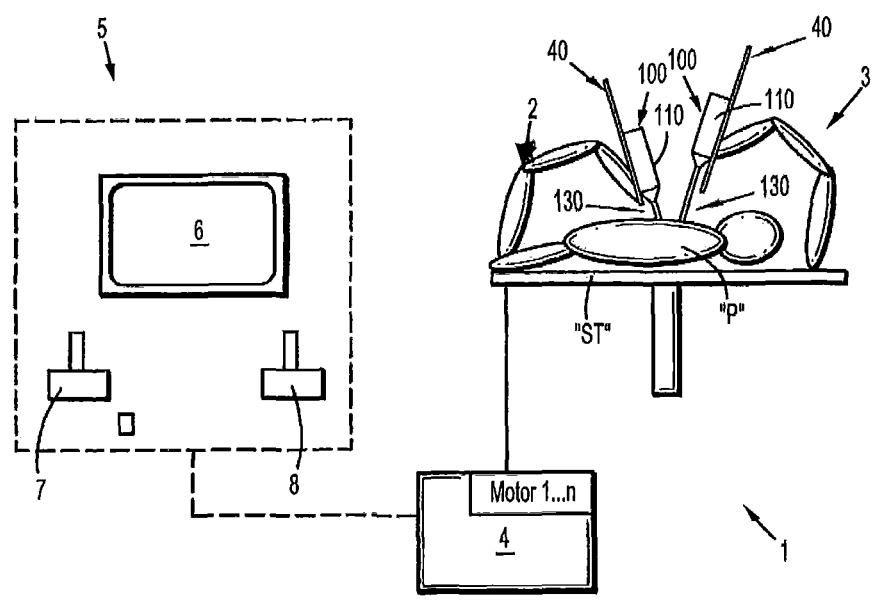
FIG. 1 is a schematic illustration of a robotic surgical system including a robotic surgical assembly in accordance with the present disclosure.

Embodiments of the presently disclosed robotic surgical system are described in detail with reference to the drawings, in which like reference numerals designate identical or corresponding elements in each of the several views. As used herein the term "distal" refers to that portion of structure that is closer to the patient, while the term "proximal" refers to that portion of structure that is farther from the patient. As used herein, the term "clinician" refers to a doctor, nurse, or other care provider and may include support personnel.

In the following description, well-known functions or constructions are not described in detail to avoid obscuring the present disclosure in unnecessary detail.

Figure 2:
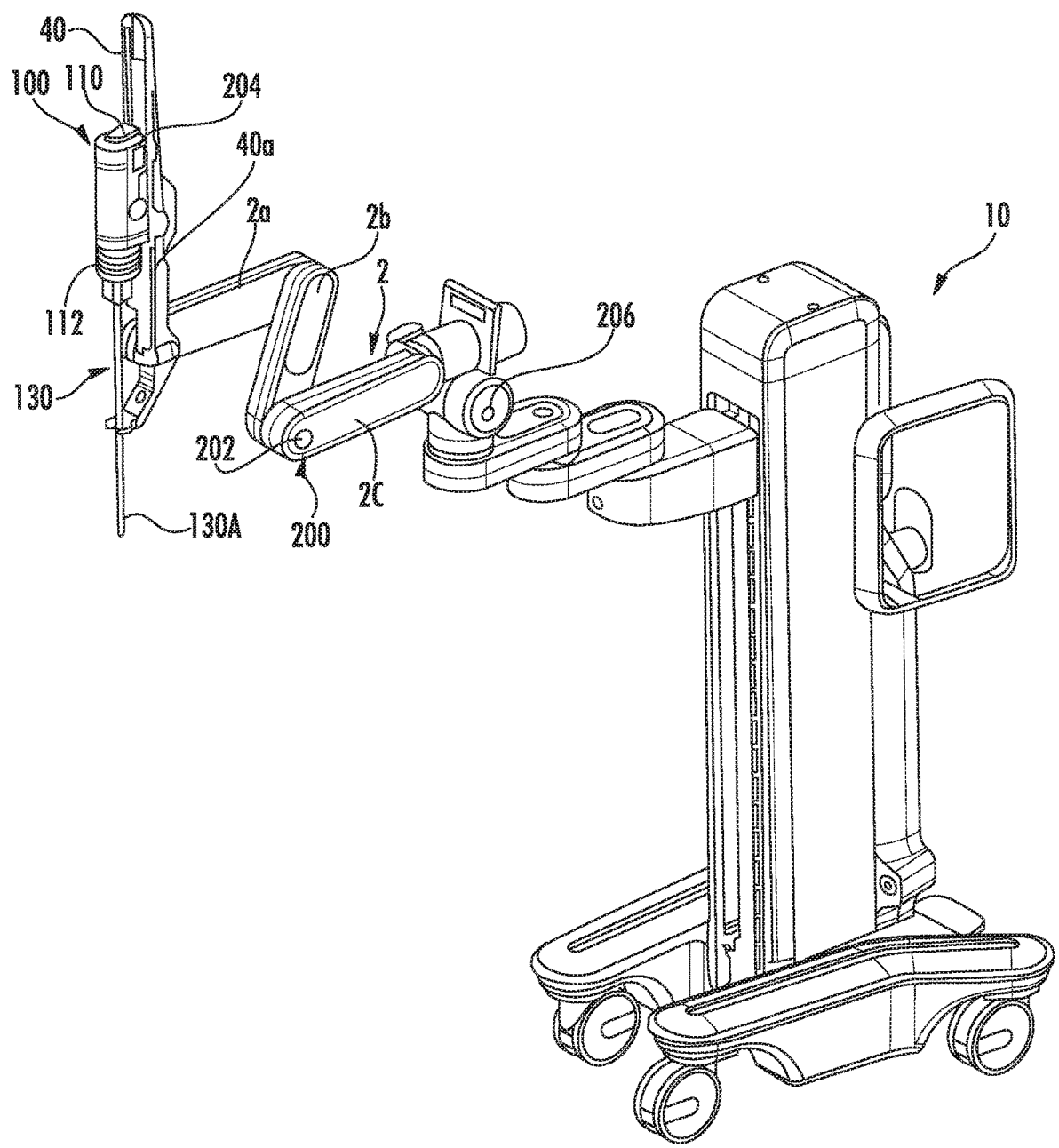
FIG. 2 is a perspective view of the robotic surgical assembly of FIG. 1 shown coupled to a robotic arm of a robotic arm cart of the robotic surgical system of FIG. 1.
Figure 3:
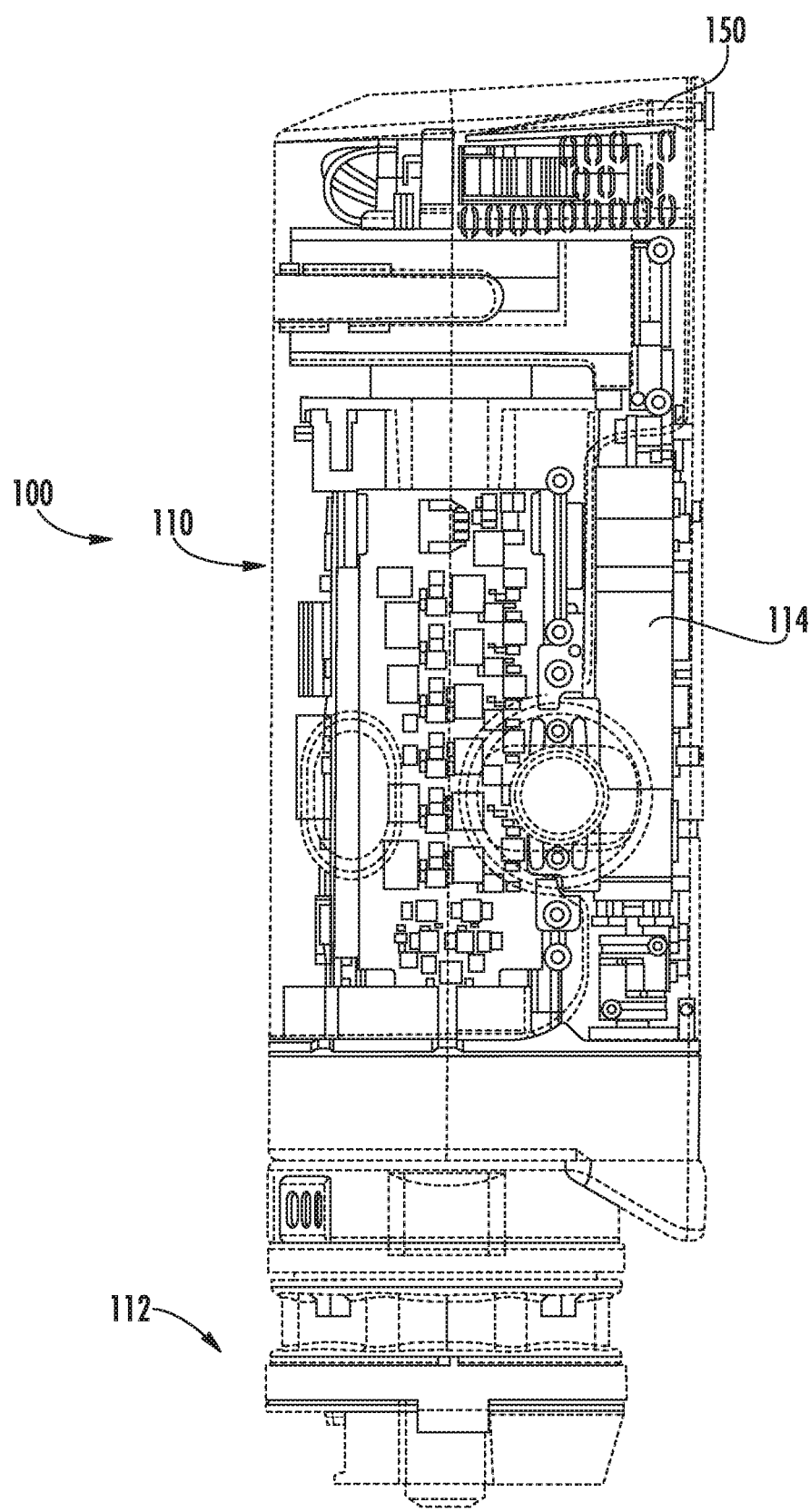
FIG. 3 is an enlarged, side view of an instrument drive unit and sterile interface module of the robotic surgical assembly of FIG. 2 with portions thereof shown in phantom for clarity.

Referring initially to FIGS. 1-3, a surgical system, such as, for example, a robotic surgical system or work station 1, generally includes a robotic arm or robotic arms 2, 3 coupled to a robotic cart 10 and a surgical assembly 100 coupled to surgical robotic arm 2. Surgical assembly 100 generally includes an instrument drive unit (hereinafter "IDU") 110 coupled to a slide rail 40 of surgical robotic arms 2, 3, and an electromechanical surgical instrument 130 operably coupled to IDU 110 by a sterile interface module 112 of surgical assembly 100.

Surgical system 1 further includes a control device 4 and an operating console 5 coupled with control device 4. Operating console 5 includes a display device 6, which is set up to display three-dimensional images; and manual input devices 7, 8, by means of which a clinician (not shown), for example a surgeon, is able to telemanipulate robotic arms 2, 3 in a first operating mode, as known in principle to a person skilled in the art. Each of robotic arms 2, 3 may be composed of a plurality of members 2a, 2b, 2c, etc., which are connected through joints. Robotic arms 2, 3 may be driven by electric drives (not shown) that are connected to control device 4. Control device 4, for instance a computer, circuit board, and/or chip, etc., may be set up to activate the drives by means of a computer program such that robotic arms 2, 3, the attached surgical assembly 100, and thus electromechanical surgical instrument 130 (including an electromechanical end effector 130a thereof), execute a desired movement according to a movement defined by means of manual input devices 7, 8. Control device 4 may also be set up in such a way that it regulates movement of robotic arms 2, 3.

Surgical system 1 is configured for use on a patient "P" lying on a surgical table "ST" to be treated in a minimally invasive manner by means of a surgical instrument, e.g., electromechanical surgical instrument 130. In embodiments, robotic arms 2, 3 may be coupled to a robotic arm cart 10 (FIG. 2) rather than surgical table "ST." Surgical system 1 may include more than two robotic arms 2, 3, the additional robotic arms likewise being connected to control device 4 and being telemanipulatable by means of operating console 5. A surgical instrument, for example, electromechanical surgical instrument 130 may also be attached to the additional robotic arm.

Control device 4 of surgical system 1 may control a plurality of motors, e.g., motors (Motor 1 . . . n), with each motor configured to drive movement of robotic arms 2, 3 in a plurality of directions. Further, control device 4 may control one or more motors or motor assemblies 114 (FIG. 3) of IDU 110 of robotic surgical assembly 100 that drive various operations of surgical instrument 130. Motors 114 of IDU 110 may include, for example, a canister motor. In embodiments, each motor 114 of IDU 110 can be configured to actuate a drive rod/cable or a lever arm (not shown) to effect operation and/or movement of electromechanical surgical instrument 130 and/or end effector 130a thereof.

For a detailed discussion of the construction and operation of a similar robotic surgical system, reference may be made to U.S. Pat. No. 8,828,023, entitled "Medical Workstation," the entire contents of which are incorporated by reference herein.

Figure 4:
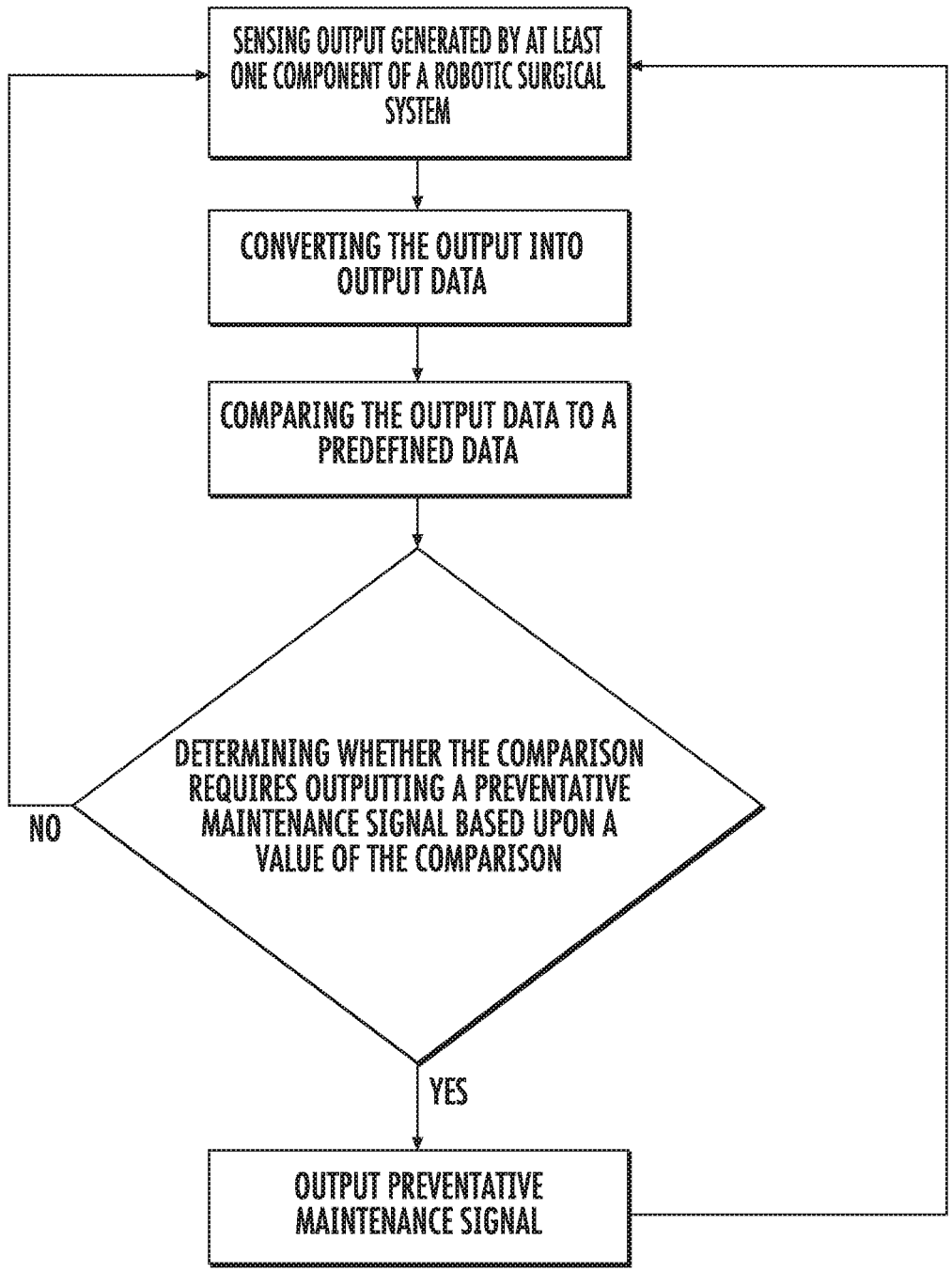
FIG. 4 is a flow chart illustrating a method for conducting preventative maintenance on a robotic surgical system.

With reference to FIGS. 1, 2 and 4, in order to more effectively schedule preventative maintenance for one or more components of surgical system 1, surgical system 1 can include any number of sensors 200, such as sensors 202, 204, 206, etc., positioned at predetermined locations on surgical system 1 for sensing output that is generated by one or more components of surgical system 1 (e.g., analog output such as audio or noise that may be generated, for example, during use or movement of one or more of the components of surgical system 1). Any number of sensors 200 (and/or placement thereof on surgical system 1) can be utilized to detect issues with performance or health of the system or components thereof. Sensors 200 may include, for example, one or more accelerometers, torque sensors, microphones, temperature sensors, encoders, etc. For instance, one or more sensors 200 can be positioned on surgical system 1 to track, for example, motor currents, motor position, output joint position, etc., or combinations thereof. Sensors 200 can be electrically coupled to control device 4, for example, to read and/or process output that is collected by one or more of sensors 200 in order to determine the health or longevity of surgical system 1, and/or the components thereof. In particular, control device 4 is configured to analyze output data of surgical system 1 that is identified and communicated by one or more of sensors 200 to more effectively establish when service is needed for surgical system 1, and/or components thereof. When control device 4 determines that service is needed a preventative maintenance signal can be output to alert service personnel to service (e.g., replace, adjust, clean, etc., or combinations thereof) surgical system 1, and/or one or more components thereof.

In embodiments, control device 4 of surgical system 1 can be configured to convert analog output into output data (e.g., audio output data) that can be analyzed by control device 4 to identify system inadequacy, wear, failure, etc., or combinations thereof. Such data conversion may involve converting analog output, such as noise or sound, from an analog signal to a digital signal for electrical communication with control device 4. Control device 4 can be configured to compare the output data, for example via the digital signal thereof, to predefined or reference data, such as predefined audio data, stored in a memory device (not shown) which may be directly or indirectly coupled to control device 4. The reference data may be provided by, or coupled to, a remote system that may be connected to surgical system 1 via internet, Bluetooth, LTE, etc., or combinations thereof. Control device 4 can be configured to selectively output a preventative maintenance signal based on a digital comparison (or multiple comparisons) of the output data to the predefined or referenced data where the comparison results in a value that indicates that one or more components failed, may be failing, require or should be replaced/adjusted, etc., and/or combinations thereof. The preventative maintenance signal can be any suitable analog or digital signal (e.g., a sound, a light, a warning message, etc., or combinations thereof).

In embodiments, data collected by one or more of sensors 200 of surgical system 1 can be compared individually, in one or more groups etc., relative to one another, and/or relative to predefined or reference data. Control device 4 and sensors 200 of surgical system 1, which are disposed in electrical communication, can be configured to cooperate to consolidate or integrate data determined by one or more of sensors 200 for more accurately generating one or more preventative maintenance signals/alerts for servicing surgical system 1 and/or one or components of surgical system 1. By analyzing data collected from multiple sources (e.g., sensor 202, sensor 204, and sensor 206), more accurate determinations can be made as to a condition, status, and/or health of surgical system 1 and/or components thereof.

For example, by collecting data from sensors 200 of motor current over time, a deduction can be made to determine if grease in a harmonic drive (not shown) of a robotic arm 2 has reached a threshold condition, such as age, use, wear, etc., to cause a reduction in efficiency. Further, by correlating collected data of motor current with running temperature, issues with electrical components (e.g., an electrical board or wiring) can be detected.

In another example, one or more of sensors 200, such as sensor 202, which may be a joint torque sensor, can be used to collect data to detect if one or more components of surgical system 1, such as robotic arm 2, was overloaded during surgery and/or to detect if there are cable stretch or cable de-tensioning issues.

In one example, data from different sensors 200, for instance sensor 206, which may be a joint encoder, and sensor 204, which may be a motor encoder, can be compared (e.g., via control device 4) to establish information on backlash, such as if it exceeds a threshold value so as to require service.

In still another example, one or more sensors 200, such as sensors 202 and/or 206, may be in the form of an accelerometer that can be utilized to detect vibrations output by surgical system 1, or components thereof, that may be caused due to a loosening of screws or the like. Data can also be collected on motor current versus acceleration to determine if service is required, for example, on a slide belt 40*a* of slide rail 40. For instance, acceleration data can be collected to determine joint forces during a back drive operation such that certain threshold forces will indicate a service requirement.

In one example, sensor 204 of surgical system 1 can be a microphone that monitors or records system audio such as fan noise generated from IDU 110. For instance, when fan 150 of IDU generates a noise (as it rotates to effectuate cooling), such noise may escalate to a predetermined threshold volume (e.g., 25 dBA) that indicates a certain amount of wear, failure, or even inadequacy that can cause control device 4 to generate a service signal for alerting service personnel to conduct preventative maintenance on fan 150 (e.g., replacement) and/or other components of surgical system 1 that may effected by the failing of fan 150.

Control device 4 of surgical system 1 can include any suitable logic control circuit adapted to perform calculations and/or operate according to a set of instructions. Control device 4 can be configured to communicate with a remote system (e.g., data warehouse over internet from hospitals), wirelessly (e.g., Wi-Fi, Bluetooth, LTE, etc.) and/or wired. The remote system can include data, instructions and/or information related to the various components, algorithms, and/or operations of surgical system 1. The remote system can include any suitable electronic service, database, platform, cloud, or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, the remote system and/or control device 4.

In some embodiments, control device 4 of surgical system 1 can include one or more counters to count, for example, a number of uses of one or more of the components of the medical surgical system. Control device 4 can include a plurality of inputs and outputs for interfacing with the components of surgical system 1, such as through a driver circuit. Control device 4 can be configured to receive input signals and/or generate output signals to control one or more of the various components (e.g., one or more motors 114) of surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to the remote system.

In embodiments, a database configured to store data can be directly and/or indirectly coupled to control device 4. The database can include memory or a memory device which can be part of, and/or or operatively coupled to, the remote system or control device 4.

In some embodiments, the memory or memory device can include reference data of the surgical system 1 and/or one or more components of surgical system 1. In some embodiments, the reference data can be predetermined or predefined. In certain embodiments, the reference data can be measured, created, or stored in real-time. The reference data can include any suitable property, characteristic and/or condition of one or more of the components of surgical system 1. In certain embodiments, the reference data may include ranges or sets of ranges to which real-time data can be compared and contrasted for determining health (e.g., expended and/or remaining lifespan). The memory may also store component reference conditions, one or more updated (real-time) component conditions, and/or other data associated with the stored conditions, such as a date that the condition was measured, created, and/or stored.

Control device 4 of surgical system 1 can be programmed to compare real-time data to reference data and provide an output signal in response to a comparison of the real-time data to the reference data. In general, referenced data/ information of the components of surgical system 1 can be stored in memory, for example, on a memory device coupled to medical surgical system 1 and/or part of a remote system as described above. Such data/information can be stored prior to any use of one or more components of surgical system 1. One or more events, (e.g., generating and storing a reference or update condition, a use and/or a number of uses of one or more components, time expiration, etc.), can occur so that real-time data of components of the surgical system 1 can be collected and/or analyzed by virtue of sensors 200 and/or control device 4, prior to, during, or after a use of surgical system 1 and/or one or more components thereof.

In certain embodiments, reference data of the one or more components can be compared with collected real-time data of the one or more components to determine the real-time health (e.g., remaining/expended lifespan) of one or more components relative to the initial, preceding, or projected health of one or more of the components. If lifespan/health of one or more of the components remains or is intact, an output signal may be provided. An occurrence of another event, which may be different and/or the same as an initial, preceding, or subsequent event, may also provide an output signal. If no health/lifespan, or a limited amount of health/ lifespan remains or is otherwise registered/intact, one or more components may fail, become unusable, or have a limited usability, which can require servicing of one or more of the components (e.g., fan 150, IDU 110, etc.) of surgical system 1. The output signal can be any suitable signal, for example, indicative of health/remaining lifespan, if any, and/or failure. As can be appreciated, stored predefined or reference data may be preset and/or updated periodically, including before, during, and/or after use.

In some aspects of the present disclosure, data processing methods can be utilized to enable control device 4 and sensors 200 to cooperate to determine when preventative maintenance should be performed. For example, fast Fourier transform algorithms can be used to convert time domain information/data to frequency domain information/data in order to analyze dominant frequencies that might correlate with the speed of rotation, which may change with wear. Another example of a data processing method includes analyzing signal amplitude changes to determine loudness. In yet another example of a data processing method, data peaks can be analyzed over time, such as during initialization routings, to report system health.

In certain aspects of the present disclosure, training models can be utilized to determine when preventative maintenance should be performed. For example, deployed systems can be used to gather data in the initial stages of implementation, and machine learning, such as neural networks, can be used to train models. In another example, deployed systems can be used to analyze use cases (e.g., position/ velocity profiles, load/current profiles, etc.).

In some aspects of the present disclosure, user interfaces can be utilized to display any of the presently disclosed data/information to the user and/or hospital utilized to determine when preventative maintenance should be performed.

In some aspects of the present disclosure, algorithms can be utilized to determine when preventative maintenance should be performed. For instance, multiple observer channels (e.g., sensors 200) can be used to record data that can be consolidated into one metric (e.g., via control device 4) such as for determining instrument lifespan.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A method of conducting preventative maintenance on a robotic surgical system that supports a surgical instrument for effectuating a surgical procedure, the method comprising:
    sensing an audio output generated by at least one component of the robotic surgical system with a sensor coupled to the robotic surgical system;
    converting the audio output into audio output data;
    comparing the audio output data to a predefined audio data stored in a memory device that is coupled to the robotic surgical system; and
    selectively outputting a preventative maintenance signal based on a comparison of the audio output data and the predefined audio data.

2. The method of claim 1, wherein sensing the audio output includes sensing a first audio output generated by an instrument drive unit of a robotic surgical system.

3. The method of claim 2, wherein sensing the first audio output includes sensing fan noise of the instrument drive unit.

4. The method of claim 2, further comprising maintaining the sensor coupled to the instrument drive unit.

5. The method of claim 1, wherein converting the audio output into the audio output data includes converting the audio output from an analog signal to a digital signal that can be electrically communicated to a control device of the robotic surgical system.

6. The method of claim 1, wherein sensing the audio output data includes recording the audio output with a microphone.

7. The method of claim 1, wherein selectively outputting the preventative maintenance signal includes determining whether the comparison requires outputting the preventative maintenance signal based upon a comparison value.

8. The method of claim 1, wherein sensing the audio output includes sensing the audio output with a plurality of sensors coupled to the robotic surgical system.

9. The method of claim 8, wherein comparing the audio output data to the predefined audio data includes comparing the audio output data from a first sensor of the plurality of sensors to the predefined audio data to generate a first comparison and comparing the audio output data from a second sensor of the plurality of sensors to the predefined audio data to generate a second comparison.

10. The method of claim 9, further comprising generating the comparison value based on the first and second comparisons.

11. A method of conducting preventative maintenance on a surgical system, the method comprising:
    sensing an audio output generated by at least one component of the surgical system with a sensor coupled to the surgical system, the surgical system supporting a surgical instrument for effectuating a surgical procedure;
    converting the audio output into audio output data;
    comparing the audio output data to a predefined audio data stored in a memory device that is coupled to the surgical system; and
    selectively outputting a preventative maintenance signal based on a comparison of the audio output data and the predefined audio data.

12. The method of claim 11, wherein sensing the audio output includes sensing a first audio output generated by an instrument drive unit of the surgical system.

13. The method of claim 12, wherein sensing the first audio output includes sensing fan noise of the instrument drive unit.

14. The method of claim 12, further comprising maintaining the sensor coupled to the instrument drive unit.

15. The method of claim 11, wherein converting the audio output into the audio output data includes converting the audio output from an analog signal to a digital signal that can be electrically communicated to a control device of the surgical system.

16. The method of claim 11, wherein sensing the audio output data includes recording the audio output with a microphone.

17. The method of claim 11, wherein selectively outputting the preventative maintenance signal includes determining whether the comparison requires outputting the preventative maintenance signal based upon a comparison value.

18. The method of claim 11, wherein sensing the audio output includes sensing the audio output with a plurality of sensors coupled to the surgical system.

19. The method of claim 18, wherein comparing the audio output data to the predefined audio data includes comparing the audio output data from a first sensor of the plurality of sensors to the predefined audio data to generate a first comparison and comparing the audio output data from a second sensor of the plurality of sensors to the predefined audio data to generate a second comparison.

20. The method of claim 19, further comprising generating the comparison value based on the first and second comparisons.

* * * * *